(12) United States Patent
Blanco et al.

(10) Patent No.: US 10,105,191 B2
(45) Date of Patent: Oct. 23, 2018

(54) MARKING TISSUE SURFACES FOR TREATMENT OF LESIONS BY ELECTRICAL NANOPULSES

(71) Applicant: PULSE BIOSCIENCES, INC., Burlingame, CA (US)

(72) Inventors: Cesar Escobar Blanco, Los Angeles, CA (US); Elena Tovkan Forster, Arcadia, CA (US); Stefani Reiko Takahashi, Pasadena, CA (US)

(73) Assignee: PULSE BIOSCIENCES, INC., Hayward, CA (US)

( * ) Notice: Subject to any disclaimer, the term of this patent is extended or adjusted under 35 U.S.C. 154(b) by 0 days.

(21) Appl. No.: 15/252,479

(22) Filed: Aug. 31, 2016

(65) Prior Publication Data

US 2017/0000584 A1 Jan. 5, 2017

Related U.S. Application Data

(63) Continuation of application No. PCT/US2015/017150, filed on Feb. 23, 2015.
(Continued)

(51) Int. Cl.
*A61B 90/30* (2016.01)
*A61B 90/00* (2016.01)
(Continued)

(52) U.S. Cl.
CPC .......... *A61B 90/39* (2016.02); *A61B 18/1206* (2013.01); *A61B 18/1402* (2013.01);
(Continued)

(58) Field of Classification Search
CPC .. B41M 3/12; A61B 90/39; A61B 2090/3904; A61B 2090/3937;
(Continued)

(56) References Cited

U.S. PATENT DOCUMENTS

2002/0041851 A1  4/2002  Kamimoto et al.
2002/0056459 A1  5/2002  Rusin et al.
(Continued)

FOREIGN PATENT DOCUMENTS

WO  2014/133870 A1  9/2014
WO  2015/134226 A1  9/2015

OTHER PUBLICATIONS

Garon et al., "In vitro and in vivo evaluation and a case report of intense nanosecond pulsed electric field as a local therapy for human malignancies," Int. J. Cancer, 2007, vol. 121, pp. 675-682.
(Continued)

*Primary Examiner* — Eric D. Bertram
(74) *Attorney, Agent, or Firm* — Kilpatrick Townsend & Stockton LLP

(57) ABSTRACT

This disclosure relates to an in vivo treatment of a skin lesion of a mammal comprising application of electrical energy to the skin lesion in a form of electrical pulses. At least one electrical pulse is applied. The pulse duration may be at least 1 nanosecond at the full-width-half-maximum. Surface of a tissue surrounding the skin lesion may be marked to guide the device to deliver the electric pulses at substantially precise locations on the lesion surface. This treatment may prevent at least growth of the lesion.

24 Claims, 14 Drawing Sheets

Related U.S. Application Data

(60) Provisional application No. 61/947,800, filed on Mar. 4, 2014.

(51) Int. Cl.
| | | |
|---|---|---|
| *A61B 18/12* | (2006.01) | |
| *A61B 18/14* | (2006.01) | |
| *A61N 1/32* | (2006.01) | |
| *A61N 1/04* | (2006.01) | |
| *A61N 1/05* | (2006.01) | |
| *A61B 18/00* | (2006.01) | |
| *A61B 17/00* | (2006.01) | |
| *A61B 5/00* | (2006.01) | |

(52) U.S. Cl.
CPC ......... *A61N 1/0468* (2013.01); *A61N 1/0502* (2013.01); *A61N 1/328* (2013.01); *A61B 5/444* (2013.01); *A61B 2017/00747* (2013.01); *A61B 2017/00774* (2013.01); *A61B 2018/00452* (2013.01); *A61B 2018/143* (2013.01); *A61B 2090/3904* (2016.02); *A61B 2090/3937* (2016.02)

(58) Field of Classification Search
CPC .... A61B 2090/3941; A61B 2090/3945; A61B 2090/395
See application file for complete search history.

(56) References Cited

U.S. PATENT DOCUMENTS

| | | |
|---|---|---|
| 2002/0114764 A1 | 8/2002 | Berryman et al. |
| 2003/0182815 A1 | 10/2003 | Carlson, II et al. |
| 2008/0171957 A1 | 7/2008 | Connolly et al. |
| 2010/0004532 A1 | 1/2010 | Bendre et al. |
| 2010/0113860 A1 | 5/2010 | Traboulsi et al. |
| 2012/0037291 A1* | 2/2012 | Goolishian ........... B44C 1/1758 156/62 |
| 2012/0059244 A1 | 3/2012 | McClelland et al. |
| 2012/0143050 A1 | 6/2012 | Heigl et al. |
| 2013/0041443 A1 | 2/2013 | Weissberg et al. |
| 2013/0138055 A1 | 5/2013 | Samlaska et al. |
| 2013/0245486 A1* | 9/2013 | Simon ................ A61N 1/36021 600/546 |

OTHER PUBLICATIONS

International Application No. PCT/US2015/017150, International Search Report and Written Opinion, dated Jun. 3, 2015, 10 pages.
Kuthi et al., "Nanosecond Pulse Generator Using a Fast Recovery Diode," Department of Electrical Engineering, 2004, 4 pages.
Tang et al., "Diode Opening Switch Based Nanosecond High Voltage Pulse Generators for Biological and Medical Applications," IEEE Transactions on Dielectrics and Electrical Insulation, Aug. 2007, vol. 14, No. 4, pp. 878-883.
Wang et al., "Solid-State High Voltage Nanosecond Pulse Generator," Jul. 2005, 5 pages.
European Application No. 15758252.9, "Extended European Search Report" dated Mar. 16, 2017, 8 pages.

* cited by examiner

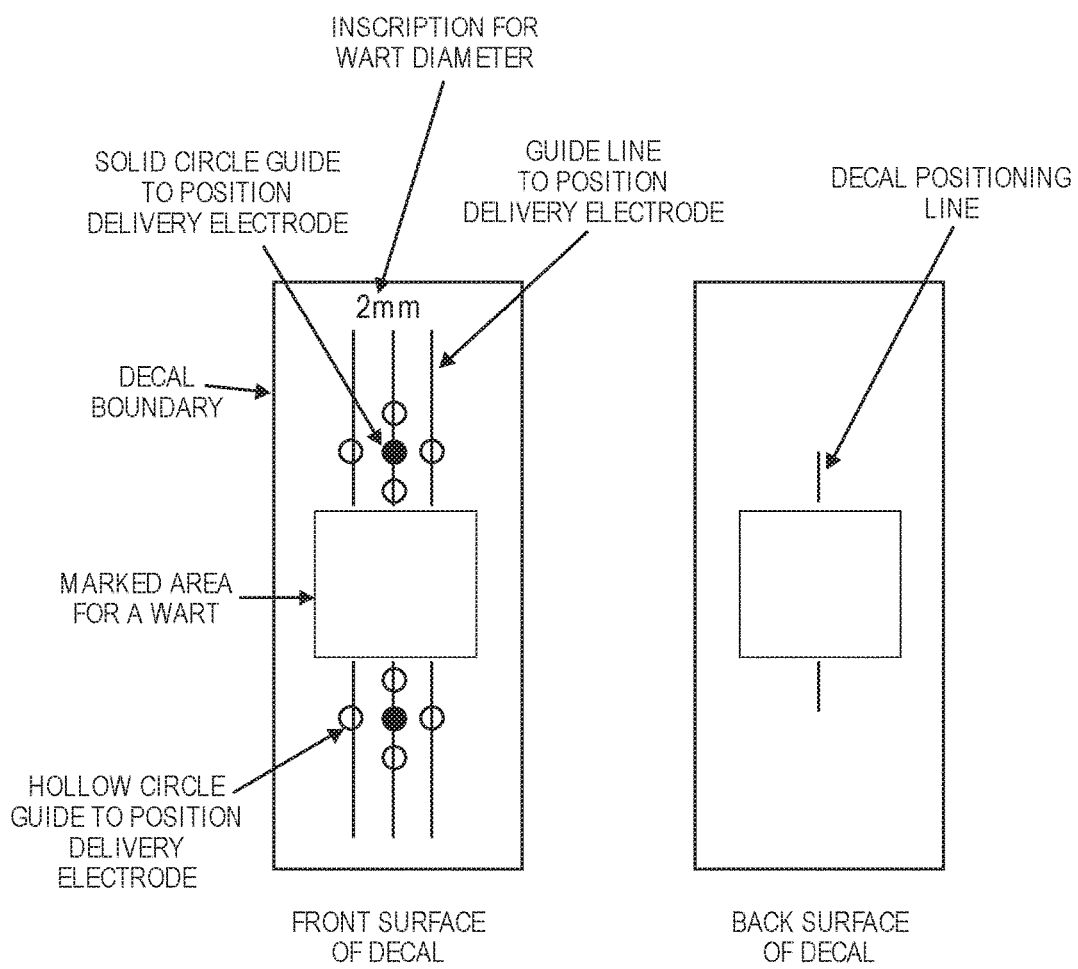
FIG. 7A  FIG. 7B

MARKING TISSUE SURFACES FOR TREATMENT OF LESIONS BY ELECTRICAL NANOPULSES

CROSS-REFERENCE TO RELATED APPLICATION

This application is a bypass continuation of International Application No. PCT/US2015/017150, filed Feb. 23, 2015, which claims priority to U.S. provisional patent application 61/947,800, entitled "Marking Tissue Surfaces for Treatment of Lesions by Electrical Nanopulses," filed Mar. 4, 2014. The entire contents of these applications are incorporated herein by reference.

BACKGROUND

Technical Field

This disclosure relates to electrical pulse generators and particularly to electrical pulse generators with insulated applicator tips. This disclosure also relates to treatment of skin lesions by delivery of electric pulses to such lesions.

Description of Related Art

Ultra-short, high-field strength electric pulses may be used in the electroperturbation of biological cells. For example, these electric pulses may be used in treatment of human cells and tissue including tumor cells such as basal cell carcinoma, squamous cell carcinoma and melanoma. For a detailed discussion of such applications, for example, see, Garon et al. "In Vitro and In Vivo Evaluation and a Case Report of Intense Nanosecond Pulsed Electric Field as a Local Therapy for Human Malignancies", Int. J. Cancer, vol. 121, 2007, pages 675-682. The entire content of this publication is incorporated herein by reference.

The voltage induced across a cell membrane may depend on the pulse length and pulse amplitude. Pulses longer than about 1 microsecond may charge the outer cell membrane and lead to opening of pores, either temporarily or permanently. Permanent openings may result in cell death.

Pulses much shorter than about 1 microsecond may affect the cell interior without adversely or permanently affecting the outer cell membrane. Such shorter pulses with a field strength in the range of 10 kV/cm to 100 kV/cm may trigger apoptosis or programmed cell death. Higher amplitude and shorter electric pulses are useful in manipulating intracellular structures such as nuclei and mitochondria.

Nanosecond high voltage pulse generators have been proposed for biological and medical applications. For example, see: Gundersen et al. "Nanosecond Pulse Generator Using a Fast Recovery Diode", IEEE 26.sup.th Power Modulator Conference, 2004, pages 603-606; Tang et al. "Solid-State High Voltage Nanosecond Pulse Generator," IEEE Pulsed Power Conference, 2005, pages 1199-1202; Tang et al. "Diode Opening Switch Based Nanosecond High Voltage Pulse Generators for Biological and Medical Applications", IEEE Transactions on Dielectrics and Electrical Insulation, Vol. 14, No. 4, 2007, pages 878-883; Yampolsky et al., "Repetitive Power Pulse Generator With Fast Rising Pulse" U.S. Pat. No. 6,831,377; Schoenbach et al. "Method and Apparatus for Intracellular Electro-Manipulation", U.S. Pat. No. 6,326,177; Gundersen et al., "Method for Intracellular Modifications Within Living Cells Using Pulsed Electric Fields", U.S. Patent Publication No. 2006/0062074; Kuthi et al., "High Voltage Nanosecond Pulse Generator Using Fast Recovery Diodes for Cell Electro-Manipulation", U.S. Pat. No. 7,767,433; Krishnaswamy et al., "Compact Subnanosecond High Voltage Pulse Generation System for Cell Electro-Manipulation", U.S. Patent Publication No. 2008/0231337; and Sanders et al. "Nanosecond Pulse Generator", U.S. Patent Publication No. 2010/0038971. Skin treatment apparatuses are also proposed. For example, see Stern "Apparatus and Method for Treatment of Tissue" U.S. Pat. No. 6,413,255. The entire content of these publications is incorporated herein by reference.

SUMMARY

This disclosure relates to a system for delivery of electrical pulses to a tissue. This system may comprise a pulse generator configured to generate at least one pulse having a duration of no more than 1,000 nanoseconds at the full-width-at-half-maximum. This system may further comprise a pulse delivery device comprising a delivery (e.g. active) electrode and a ground (i.e. return, at or near ground potential) electrode. Each of the delivery electrode and the ground electrode has an outer surface.

The system may generate at least one pulse of a duration of no more than 100 nanoseconds at the full-width-at-half-maximum. The system may be configured to generate at least one pulse with an amplitude of at least 1 kV. The electric field formed by the pulses may be at least 1 kV/cm.

In one example, the at least one delivery electrode and/or the at least ground electrode may partially or substantially penetrate the tissue. In another example, the at least one delivery electrode and/or the at least one ground electrode may be configured not to substantially penetrate a tissue. In yet another example, the at least one ground electrode may be configured not to substantially penetrate a tissue.

The pulse delivery device may also comprise an electrode array. The electrode array may comprise at least two delivery electrodes and at least two ground electrodes.

This disclosure also relates to a treatment of a skin lesion of a mammal comprising application of electrical energy to the skin lesion in the form of at least one electrical pulse by using the system. Multiple pulses may also be applied. The pulse duration may be no longer than 1,000 nanoseconds at the full-width-half-maximum. The energy may be applied in a manner that may prevent at least growth of the lesion.

The skin lesion may be any deviation of skin from a healthy or a normal condition. Examples of skin lesions include skin diseases, conditions, injuries, defects, abnormalities or combinations thereof. For example, such skin lesions include malignancies (such as basal cell carcinomas, squamous cell carcinomas and melanoma), precancerous lesions (such as actinic keratosis), human papilloma virus (HPV) infected cells (such as verruca vulgaris or common warts, plantar warts, genital warts), immune-related conditions (such as psoriasis), other skin abnormalities (such as seborrheic keratosis and acrochordon); molluscan contagiosum or combinations thereof. In one example, the skin lesion is basal cell carcinoma, papilloma, squamous cell carcinoma, actinic keratosis, warts or combinations thereof. The skin lesion may also comprise common warts. Or the skin lesion may also comprise actinic keratosis.

The applied electrical energy may be sufficient to prevent growth of the skin lesion for a duration of at least one week after the treatment. The applied electrical energy may be sufficient to reduce the skin lesion volume by at least 30% within eight days after the treatment. The skin lesion volume reduction may be at least 50% or even be at least 80%. The applied electrical energy may be sufficient to clear the skin lesion within eight days after the treatment. The applied energy may be sufficient to reduce the skin lesion volume within eight days after the treatment for at least 80% of cases. The applied energy may be sufficient to reduce the skin lesion volume by at least 30% within eight days after the treatment for at least 80% of cases. The applied energy may eliminate (i.e. clear) the skin lesion.

The duration of the at least one electrical pulse at the full-width-half-maximum may be in the range of 1 nanosecond to 100 nanoseconds. The duration of the at least one electrical pulse at the full-width-half-maximum may be in the range of 1 nanosecond to 30 nanoseconds.

The applied electrical energy may be at least 65 mJ per $mm^3$ of the skin lesion. It may also be at least 260.0 $mJ/mm^3$ or at least 520.0 $mJ/mm^3$.

The system may generate at least one electrical pulse with an amplitude of at least 1 kV. This pulse forms an electric field between the at least one delivery electrode and the at least one ground electrode. The electric field formed by each pulse may be at least 1 kV/cm at the peak amplitude of the pulse. The electric field formed by each pulse may be in the range of 1 kV/cm to 1,000 kV/cm at the peak amplitude of the pulse. The electric field formed by each pulse may be in the range of 1 kV/cm to 100 kV/cm at the peak amplitude of the pulse. The electric field formed by each pulse may be in the range of 10 kV/cm to 50 kV/cm at the peak amplitude of the pulse.

The system may apply at least 10 pulses, 100 pulses or 1,000 pulses.

This disclosure relates to a decal. The decal may comprise a film that may be transferable to a surface of an object that is visibly different than other regions of the object surface ("visibly different region") and that has a size. For example, the visibly different region may be a skin lesion and the object is a skin of a human. The decal may further comprise a guide mark ("decal positioning mark") that is usable to position the decal on the object surface. The decal may also further comprise another guide mark ("device guiding mark") on the film that is transferable to the object surface together with the film and that is usable to position a device in relation to the object surface after the film is transferred to the object surface. The decal positioning mark may be on the back surface of the decal.

In another example, the decal may further comprise another guide mark ("marked area") on the decal. After the film is transferred on the surface, the marked area may be usable to indicate a boundary around the visibly different region on the object surface. The marked area may not comprise the film (in other words, free of the film).

The decal has a front surface and a back surface. The film has a front surface and a back surface. The front surface of the film may have a configuration that causes it to be in contact with the object surface after the film is transferred to the object surface. The film and the device guiding mark may have a configuration that causes them to detachably attach to the object surface after the film is transferred to the object surface.

In one example, the decal may further comprise a substrate to which the film is detachably attached before it is transferred to the object surface.

In another example, the decal may further comprise an inscription indicating a size ("inscription size") of the visibly different region.

This disclosure also relates to a system. The system may comprise a device ("pulse delivery device") and a decal that is usable to position the pulse delivery device in relation to the object surface after the film is transferred to the object surface. The pulse delivery device may be any pulse delivery device. For example, the pulse delivery device disclosed above may be used for this purpose. In another example, the pulse delivery device may comprise at least one delivery electrode. The pulse delivery device may deliver at least one electrical pulse to the visibly different region after the film is transferred to the object surface. The at least one electrical pulse may have a duration of no longer than 1,000 nanoseconds at full-width-at-half-maximum. In one example, the decal may further comprises an inscription indicating a size ("inscription size") of the visibly different region.

In another example, the pulse delivery device may further comprise at least one ground electrode. Both the delivery electrode and the ground electrode have distal ends. The device guiding marks may be configured such that, after the device guiding marks are transferred to the skin, the device guiding marks are aligned with the distal ends of the delivery electrode and the ground electrode, when these distal ends are brought in contact with the object surface.

In another example, the pulse delivery device may further comprise a guide mark ("device alignment mark") that is usable with the device guiding mark to position the at least one delivery electrode in relation to the visibly different region, before delivery of at least one electrical pulse.

In one example, the system may further comprise a power supply, a controller, and a pulse generator. The power supply may provide electrical power to both the controller and the pulse generator. The controller may provide control signals to both the controller and the pulse generator. The pulse generator may generate at least one electrical pulse with a duration of no longer than 1,000 nanoseconds at full-width-at-half-maximum and may deliver the at least one electrical pulse to the pulse delivery device.

This disclosure also relates to a method of delivering one or more electrical nanopulses to a lesion on a surface of a skin. This method may comprise providing a system comprising a pulse delivery device, providing a decal, positioning the pulse delivery device using the decal, and delivering at least one electrical pulse to the lesion using the pulse delivery device.

In one example, the method may further comprise debriding the skin lesion before delivering at least one electrical pulse to the lesion.

In another example, the method may further comprise providing the decal with a guide mark ("the decal positioning mark"), and using the decal positioning mark to position the decal in relation to the lesion before positioning the pulse delivery device.

The lesion may have a center. The center of the lesion may be marked to position the decal and/or the pulse delivery device in relation to the lesion.

In another example, the method may further comprise providing the decal with a guide mark ("device guiding mark"), transferring the device guiding mark to the skin surface, positioning the pulse delivery device using the device guiding mark before delivering at least one electrical pulse to the lesion.

The device guiding mark may detachably attach to the tissue surface on a region surrounding the lesion.

In one example, the pulse delivery device may further comprise a guide mark ("device alignment mark") that is usable together with the decal to position the pulse delivery device. In another example, the pulse delivery device may further comprise a guide mark ("device alignment mark") that is usable together with the device guiding mark to position the pulse delivery device.

The method may use any type of decal. For example, this method may use any decal disclosed above.

The method may use any system to deliver electric pulses. For example, this method may use any system disclosed above.

In one example, the decal may further comprise an inscription indicating a size of the lesion ("inscription size").

Any method disclosed above may be used to deliver electric pulses to a lesion. The lesion may be any lesion. For example, the lesion may be a wart of a human.

Any combination of above systems, devices, and methods are within the scope of this disclosure.

These, as well as other components, steps, features, objects, benefits, and advantages, will now become clear from a review of the following detailed description of illustrative embodiments, the accompanying drawings, and the claims.

BRIEF DESCRIPTION OF DRAWINGS

The drawings disclose illustrative embodiments. They do not set forth all embodiments. Other embodiments may be used in addition or instead. Details which may be apparent or unnecessary may be omitted to save space or for more effective illustration. Conversely, some embodiments may be practiced without all of the details which are disclosed. When the same numeral appears in different drawings, it refers to the same or like components or steps.

FIGS. 7A-7C: Example of a decal suitable for a treatment of about 2 mm diameter lesions, including: 7A front surface of decal, 7B back surface of decal, and 7C after film is transferred to the skin surface. The silhouette of the applicator tip is not part of the decal and shown only for demonstrative purposes.

DETAILED DESCRIPTION OF ILLUSTRATIVE EMBODIMENTS

Figure 1:
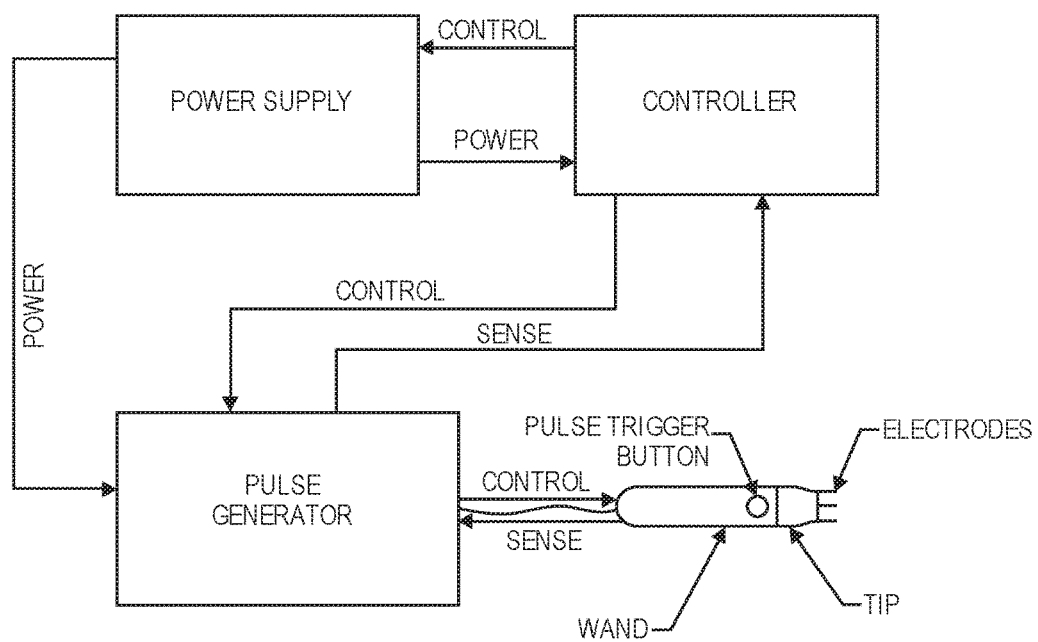
FIG. 1: Example of a system for generation and delivery of electrical nanopulses to a skin lesion.

Illustrative embodiments are now discussed. Other embodiments may be used in addition or instead. Details which may be apparent or unnecessary may be omitted to save space or for a more effective presentation. Conversely, some embodiments may be practiced without all of the details which are disclosed.

This disclosure relates to an in vivo treatment of skin lesions of mammals by application of at least one electrical pulse with a duration of 1,000 nanoseconds or less as measured at the full-width-half-maximum (FWHM) of the pulse.

The skin lesion that may be treated in vivo by the devices described herein may be any deviation of skin from a healthy or a normal condition. Examples of the skin lesions include skin diseases, conditions, injuries, defects, abnormalities or combinations thereof. For example, such skin lesions may be malignancies (such as basal cell carcinomas, squamous cell carcinoma and melanoma), precancerous lesions (such as actinic keratosis), human papilloma virus (HPV) infected cells (such as verruca vulgaris or common warts, plantar warts, genital warts), immune-related conditions (such as psoriasis), other skin abnormalities (such as seborrheic keratosis and acrocordon) and combinations thereof. The skin lesion may also include aged skin, wrinkled skin or damaged skin. An example of the damaged skin is skin damaged by sun radiation. In one example, the skin lesions may be basal cell carcinoma (including papilloma), squamous cell carcinoma, actinic keratosis, warts, or combinations thereof. In one example, the skin lesion may be a skin lesion of a human. In another example, the skin lesion may comprise basal cell carcinoma, squamous cell carcinoma, actinic keratosis, warts, or combinations thereof. In another example, the skin lesion may also comprise common warts, actinic keratosis, or combinations thereof. The skin lesion may be a common wart of a human. The skin lesion may also be an actinic keratosis of a human.

The skin lesion may form a visibly different region on the skin.

The in vivo treatment may be achieved by providing electrical energy to the skin lesion in a form of electrical pulses. During this treatment, tissue removal may not be intentional and, if it happens, may not be substantial. Thus, the treatment may thereby be advantageous over current or other proposed treatment techniques, since it may achieve its purpose with no substantial tissue removal.

The in vivo treatment of the skin lesion may prevent growth of the lesion. In one example, the treatment may reduce the volume of the skin lesion. That is, the treatment may induce shrinkage of the lesion. This shrinkage may be at least 10%, 20%, 30%, 60%, 70%, 80%, or 90%. Yet, in another example, it may be a treatment to reduce the skin lesion volume to a negligible level (i.e. clearance of the lesion). In yet other examples, the lesion growth prevention or the lesion volume reduction may be achieved in at least 10%, 20%, 30%, 40%, 50%, 60%, 70%, 80%, or 90% of the cases.

When the lesion volume shrinks to a negligible size (i.e. about 100%), the lesion is "cleared". If the lesion growth or shrinkage is less than 10% after the treatment, the lesion growth is considered to have been "prevented" or that there is "no change". If the lesion shrinkage is in the range of >10% and <50%, it is concluded that there is lesion "shrinkage". If the lesion shrinkage is in the range of >50% and <100%, it is concluded that there is "substantial shrinkage". If the lesion growth is in the range of >10% to <100%, it is concluded that there is lesion "growth". And if the lesion growth is >100%, it is concluded that there is "substantial growth".

The treatment results may be permanent or temporary. In one example, the growth prevention, or the shrinkage or the clearance may last for a duration of at least 7 days, at least 10 days, at least 20 days, at least 30 days, at least 40 days, at least 50 days, at least 60 days, at least 70 days, at least 80 days, at least 90 days, at least 100 days, or at least 110 days.

Any system may be used for delivery of electrical nanopulses with a duration of 1,000 nanoseconds or less at FWHM to the skin lesion.

The system may comprise a power supply, a controller, a pulse generator, and a pulse delivery device (e.g., a wand). An example of this system is schematically shown in FIG. 1.

The pulse generator may be any pulse generator that is capable of generating pulses with a duration of 1,000 nanoseconds or less at FWHM. Examples of such pulse generators are disclosed in Kuthi et al., "High Voltage Nanosecond Pulse Generator Using Fast Recovery Diodes for Cell Electro-Manipulation", U.S. Pat. No. 7,767,433; Sanders et al. "Nanosecond Pulse Generator", U.S. Patent Publication No. 2010/0038971; and Schoenbach et al. "Method and Apparatus for Intracellular Electro-Manipulation", U.S. Pat. No. 6,326,177. The entire content of these patents and patent publication is incorporated herein by reference.

The pulse delivery device may be any device that can deliver the electrical pulses to the skin lesion. This device may comprise an applicator tip that may comprise at least one delivery (e.g. active) electrode. This applicator may further comprise at least one ground (i.e. return, at or near ground potential) electrode. In one example, the delivery electrode and/or the ground electrode may penetrate into the skin lesion to deliver the electrical pulses. In another example, the delivery electrode and/or the ground electrode may deliver the electrical pulses without substantially or intentionally penetrating into the skin lesion. For example, the skin lesion may be constricted between the electrodes or the electrodes may only touch the lesion during the delivery of the electrical pulses.

Figure 4:
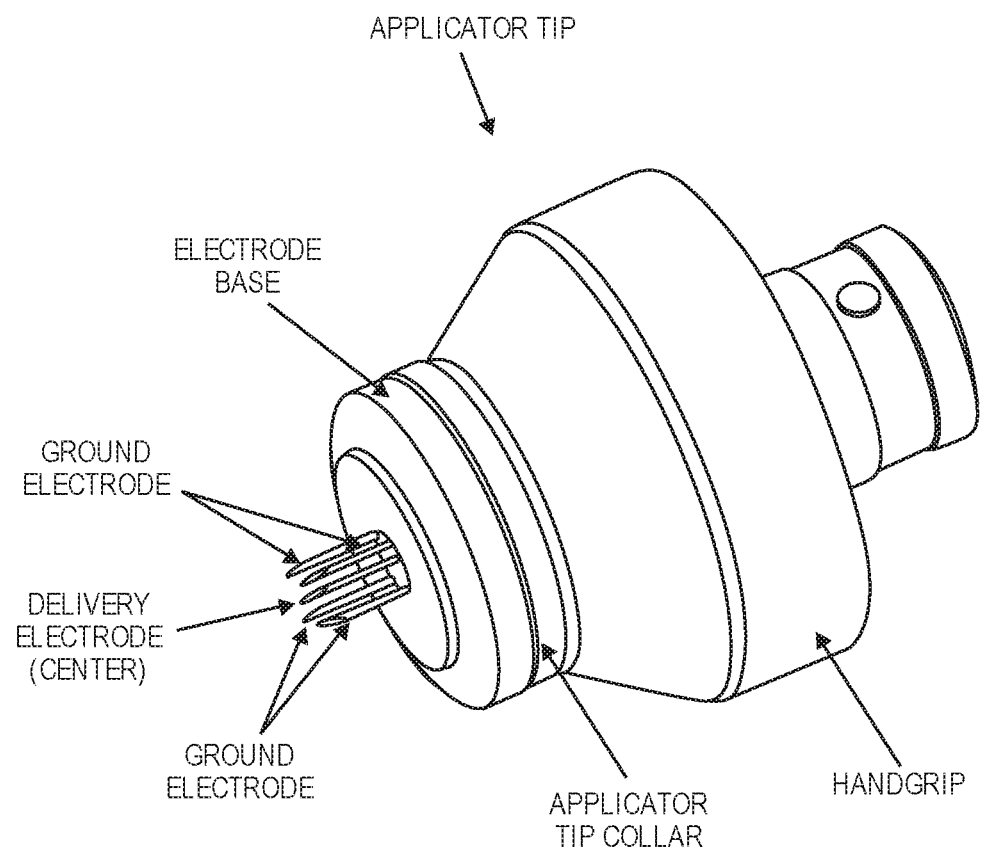
FIG. 4: Example of an applicator tip with one delivery electrode and four ground electrodes.

An example of the applicator tip is illustrated in FIG. 4. In this example, the applicator tip has one delivery electrode placed at the center and four ground electrodes surrounding the delivery electrode. The base of the electrodes may be embedded in a solid insulating material to maintain separations between them.

Other tip configurations may be used instead. There may be other applicator tip configurations suitable for the treatment of the lesions. These configurations may include tips comprising at least one delivery electrode and at least one ground electrode. For example, as the system disclosed above is coaxial in nature, with the ground electrodes surrounding the delivery electrode, any number of needle configurations may be realized, including a circular arrangement with five or more ground electrodes, a triangular arrangement with three ground electrodes, wherein the delivery electrode may be placed at the geometrical center of such arrangements. A simple linear arrangement with just two opposing electrodes, i.e., one return electrode and one delivery electrode, may also be used for the delivery of the electrical pulses.

Still other tip configurations, for example those with different electrode spacing or length, may also be used for the treatment of the lesions. However, as the effect of these short pulses on cells is largely dependent upon the strength of the electric field, an increase in the return and active electrode spacing may have to be accompanied by a proportional increase in output voltage to maintain the required field for the effect on cells. Similarly, if the spacing is reduced, the voltage could be proportionally decreased.

An array of above ground electrode and delivery electrode configurations may also be used to construct a tip and deliver the electrical pulses to the skin lesions. For example, an electrode array comprising at least two delivery electrodes and at least two ground electrodes may be used for this purpose.

The electrical energy may be applied to the skin lesion in the form of at least one electrical pulse. In one example, at least 10 pulses, at least 100 pulses or at least 1,000 pulses may be applied to treat the lesion during a single treatment.

In one example, the duration of one or more of the pulses at FWHM may be in the range of 0.01 ns to 1,000 ns. The duration of one or more of the pulses at FWHM may also be in the range of 1 ns to 100 ns or in the range of 1 ns to 30 ns. The frequency of pulses may be in the range of 0.1 Hertz (Hz) to 100,000 Hz. The frequency of pulses may also be in the range of 1 Hz to 1,000 Hz.

The electrical energy applied per volume of the skin lesion may be at least 65 $mJ/mm^3$. The applied electrical energy per volume of the skin lesion may also be at least 260 $mJ/mm^3$. In yet another example, the applied electrical energy per volume of the skin lesion may also be at least 520 $mJ/mm^3$.

The electric pulse forms an electric field between the at least one delivery electrode and the at least one ground electrode. The formation of this electric field in the tissue may prevent at least the growth of the lesion. This electric field may also cause shrinkage or clearance of the lesion. The electric field formed by each pulse may be at least 1 kV/cm at the peak amplitude of the pulse. The electric field formed by each pulse may also be in the range of 1 kV/cm to 1,000 kV/cm at the peak amplitude of the pulse. Yet, in another example, the electric field formed by each pulse may be in the range of 1 kV/cm to 100 kV/cm at the peak amplitude of the pulse. The electric field formed by each pulse may also be in the range of 10 kV/cm to 50 kV/cm at the peak amplitude of the pulse.

EXAMPLE 1

Nanopulse Generator and Electrical Nanopulses

An electrical pulse generation and delivery system, schematically shown in FIG. 1, comprising a pulse generator was constructed at the Alfred E. Mann Institute for Biomedical Engineering at the University of Southern California (Los Angeles, Calif.). In this system, the controller provided control signals to both the power supply and the pulse generator. The power supply provided power to both the controller and the pulse generator. And the pulse generator generated high voltage nanosecond pulses. The wand comprised a pulse trigger button and a tip with electrodes. The pulse trigger button controls the delivery of the pulses from the pulse generator.

Figure 2:
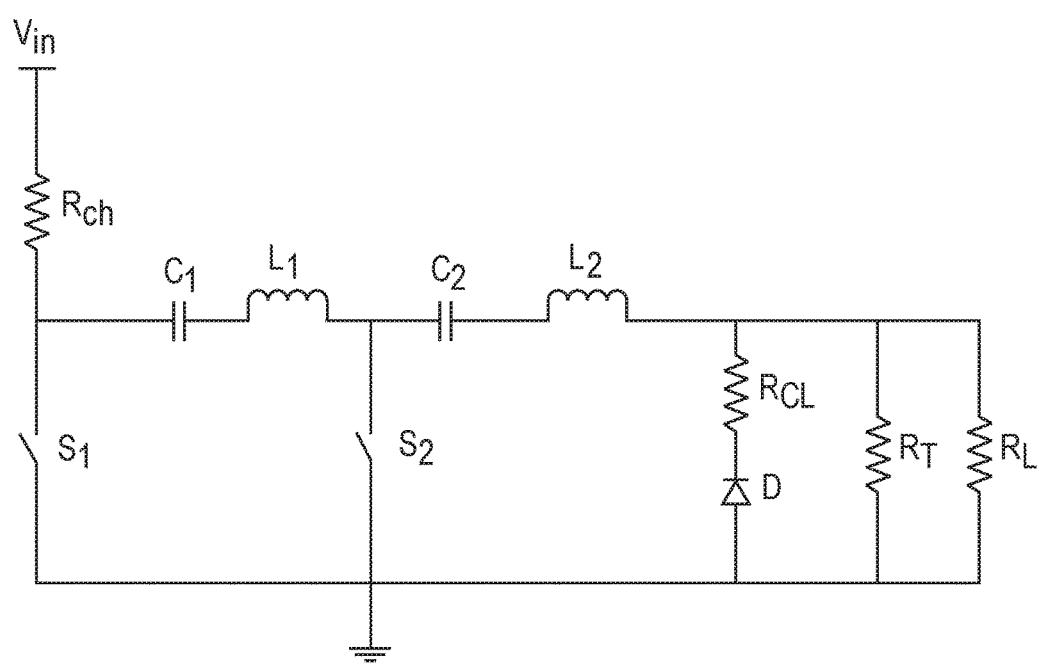
FIG. 2: Example of a simplified diode pulse generator.

An example of the pulse generator is schematically shown in FIG. 2. This pulse generator was previously disclosed in detail in U.S. Pat. No. 7,767,433 to Kuthi et al. and in U.S. Patent Application U.S. 2010/0038971 to Sanders, the content of which is incorporated by reference. This pulse generator is briefly described below.

As shown in FIG. 2, the diode pulse generator may include a tank circuit consisting of inductances $L_1$ and $L_2$ and capacitances $C_1$ and $C_2$. The tank circuit may be connected in series with a diode D across which a load $R_L$ to be driven may be connected. This load is the resistance of the lesion or tissue. The pulse generator may include a switching system, such as switches $S_1$ and $S_2$, which may be electronic. A voltage supply $V_{in}$ may be connected to the diode pulse generator through a resistance $R_{ch}$.

Before the beginning of a pulse cycle, the switch $S_1$ may be open and the switch $S_2$ may be closed. This may cause the capacitance $C_1$ to fully charge and the capacitance $C_2$ to fully discharge.

At the beginning of the pulse cycle, the switch $S_1$ may be closed and the switch $S_2$ may be opened. This may cause charge to transfer from the capacitance $C_1$ to the capacitance $C_2$. During this transfer, the current through the tank circuit may rise and fall in approximately a sinusoidal manner.

This current may cause the diode D to be forward-biased as it travels through it. During this process, charge may be stored in the depletion layer of the diode D.

At the end of the half-cycle, switch $S_2$ may be closed. During the next half-cycle, the current flow may reverse in direction, causing the diode D to be reverse-biased. During the first part of the second half-cycle, current may still flow through the diode D while charge in its depletion layer is being depleted. Once the charge is depleted, the current through the diode D stops, causing the diode to appear as an open switch. This may cause the current through the inductance $L_2$ to commute from the diode D to the load $R_L$. The diode D may thus be configured to act as an opening switch, interrupting the current in the inductance $L_2$ and commuting it into the load $R_L$.

Current may now travel through the load $R_L$ until the energy stored in the tank circuit consisting of the capacitance $C_2$ and the inductance $L_2$ depletes, thus delivering a pulse into the load $R_L$.

This pulse generator included a current limiting resistor, $R_{ch}$ configured to limit damage to the pulse generator. The value of this resistor was of about 1 ohm. The pulse generator further included a terminating resistance, $R_T$ in parallel with the diode D, wherein the terminating resistance was configured to protect the output stage of the pulse generator. The value of this resistor was about 100 ohms.

Figure 3:
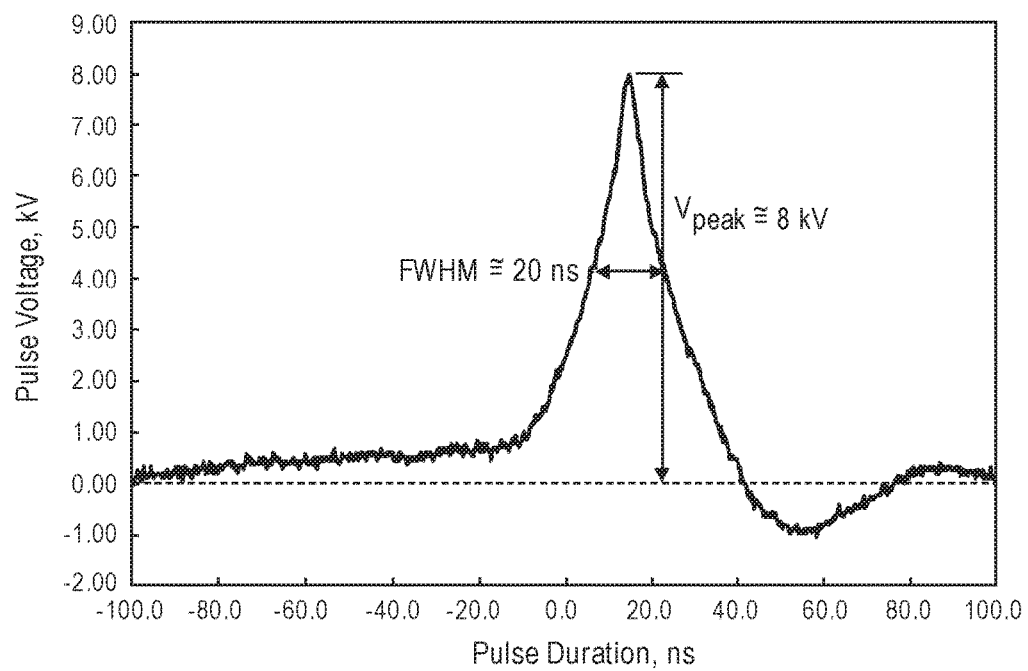
FIG. 3: Example of an electrical pulse generated by the system shown in FIG. 1.

The pulse generator disclosed above provided at least one electrical pulse with a duration varying in the range of about 7 nanoseconds (ns) at FWHM to about 20 ns at FWHM. In one example, a pulse with duration of about 20 ns at FWHM was generated. The characteristics of this pulse were recorded by an oscilloscope manufactured by Tektronix (Beaverton, Oreg.) with a model number of DPO4104. As shown in FIG. 3, this pulse had a pulse duration of about 20 ns at FWHM and a peak amplitude of about 8.00 kV.

The electrical nanopulses were delivered to a lesion by using an applicator tip comprising one delivery electrode and four ground electrodes surrounding the delivery electrode. This applicator tip is shown in FIG. 4. Each electrode was constructed by using a 30 gauge needle (i.e. 0.255 millimeters in diameter). These needles were manufactured by using a 316 LVM implant grade stainless steel material suitable for medical applications. The length of the each electrode was about 5 millimeters (mm). The electrodes were placed to form a square pattern. The ground electrodes were at the corners of this square and the delivery electrode was at its center. The ground electrodes attached to a metal base plate, which also was manufactured by using a 316 LVM implant grade stainless steel material suitable for medical applications. Center-to-center distance between the delivery electrode and each ground electrode was about 1.75 millimeters (mm). This configuration provided a volume of about 30.625 cubic millimeters ($mm^3$) within the boundary formed by the ground electrodes. The ground electrodes and the delivery electrode were electrically isolated (i.e. separated) from each other by embedding them in a Teflon insulation (not shown in FIG. 4).

The pulse generator disclosed above provided at least one electrical pulse with a duration of about 14 nanoseconds at FHWM. Each pulse with a duration of about 14 nanoseconds at FHWM contained significant frequency components centered at about 71.4 megahertz (MHz). Each such pulse had a peak amplitude of about 7.0 kilovolts (kV). These pulses were generated with a frequency of about 50 pulses per second. The electric field was in the range of 20 kilovolts/centimeter (kV/cm) to 40 kV/cm between the delivery electrode and each of the ground electrode at the peak amplitude of about 7.0 kV.

Values of the pulse durations and the peak amplitudes disclosed in this document are average values unless otherwise specifically indicated. These pulse durations and peak amplitudes may vary with a standard deviation of 10% of their average values. For example, the pulse duration of about 14 ns at FWHM may be an average of pulse durations that vary within the range of 12.60 ns and 15.40 ns, or it is 14.00±1.40 ns. Similarly, the peak amplitude of about 7.00 kV may be an average of the peak amplitudes that vary within the range of 6.30 kV and 7.70 KV, or it is 7.00±0.70 kV.

Electrical power delivered by the applicator tip at the peak of the pulse, $P_{peak}$ is:

$$P_{peak} = V_{peak}^2 / R_L \qquad \text{Equation 1}$$

where, $V_{peak}$ is the peak amplitude of electrical potential. $R_L$ was fixed at about 100 ohms when the pulse generator was configured. That is, the lesion resistance was expected to be about 100 ohms.

The electrical energy delivered by the applicator tip per pulse, $E_p$ is:

$$E_p = (2 \times P_{peak} \times t_{FHWM})/3 \qquad \text{Equation 2}$$

where, $t_{FHWM}$ is the pulse duration at FWHM.

Then, for RL of about 100 ohms and Vpeak of about 7.00 kV, the total energy delivered to the tissue per pulse was calculated to be about 2.29 millijoules (mJ) for the pulse duration of about 7 ns at FWHM, about 4.57 mJ for the pulse duration of about 14 ns at FWHM, or about 5.88 mJ for the pulse duration of about 18 ns at FWHM. For RL of about 100 ohms and Vpeak of about 5.5 kV, the total energy delivered to the tissue per pulse was calculated to be about 2.82 mJ for the pulse duration of about 14 ns at FWHM.

EXAMPLE 2

Non-Penetrating Applicator Tip

In this example, non-penetrating applicator tips are described. Such tips are disclosed in detail in an international patent application filed under the PCT; with a title "Electric Pulse Generators with Non-Penetrating Applicator Tips", and application number PCT/US14/17453 to Weissberg et al., the entire content of which is incorporated herein by reference. This pulse generator and the pulse delivery device are briefly described below.

The pulse delivery device of this example may be any device that can deliver the electrical pulses to the skin lesion. This device may comprise at least one delivery (e.g. active) electrode. This device may further comprise at least one ground (i.e. return, at or near ground potential) electrode. This device may further comprise an electrical insulation between the at least one delivery electrode and the at least one ground electrode. Both the at least one delivery electrode and the at least one ground electrode may deliver the electrical pulses without substantially penetrating the said electrodes into the skin lesion, below its surface. For example, the at least one delivery electrode, the at least one ground electrode, and the electrical insulation may each have a distal end that collectively form a substantially smooth surface that will not penetrate the tissue when pressed against the tissue with pressure sufficient to form an electrical connection between the tissue and the distal ends of the at least one delivery electrode and the at least one ground electrode. For example, this substantially smooth surface may be a substantially flat surface. In an example of the substantially flat surface, the electrodes may slightly protrude from a substantially flat surface. This slight protrusion may be no longer than 0.5 mm, 1 mm or 2 mm. In another example, the substantially smooth surface is a curved surface. For example, the curved surface is a convex surface or a concave surface or a surface that is in part a concave surface and in part a convex surface (like cyma reversa).

An example of the distal end of the electrical pulse delivery device with a substantially smooth at its distal end is illustrated in FIGS. 5A-5B. In this example, the distal end is a cylinder and the non-penetrating surface is substantially flat. This electrical pulse delivery device has one delivery electrode placed at the center and one ground electrode surrounding the delivery electrode, forming a complete "ring". The space between the delivery electrode and the ground electrode is filled with an electrically insulating material, such as teflon or a metal oxide.

EXAMPLE 3

Skin Lesion

Figure 6:
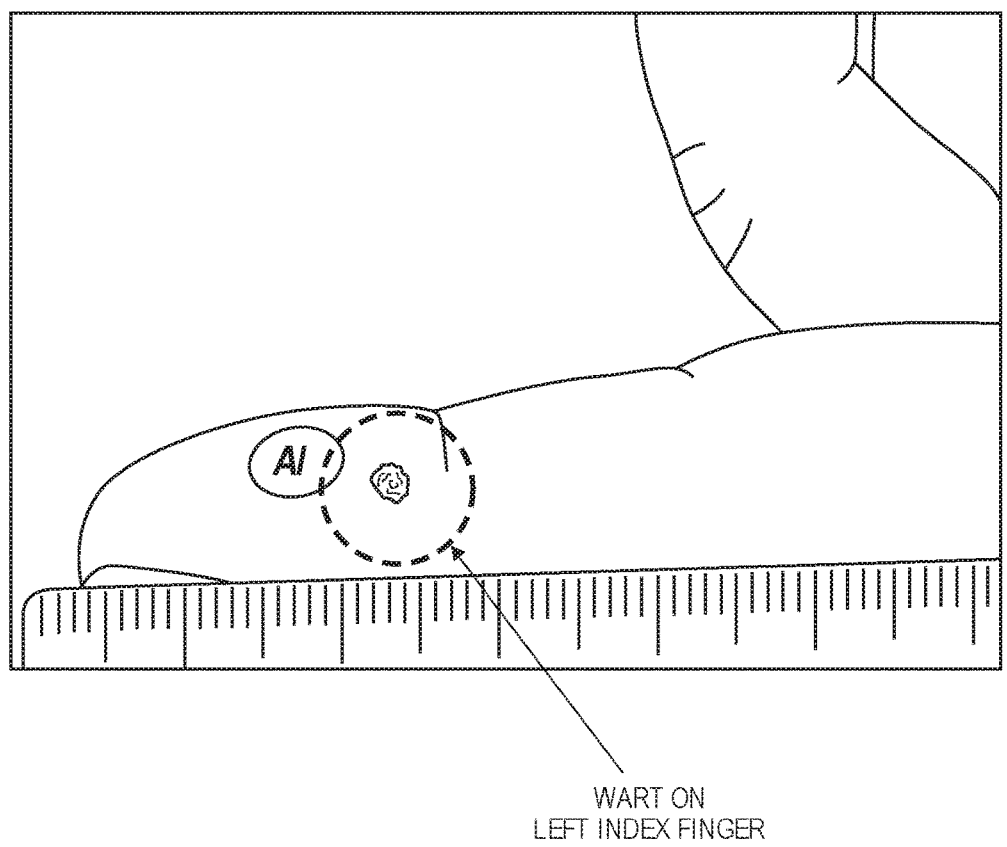
FIG. 6: Traced photograph of an exemplary lesion on a human's left index finger.

An example of a wart formed on a human's left index finger is shown in FIG. 6. The area covered by the wart was visually determined by clinical personnel. Measurements were carried out by using ruler. The highest elevation of the wart as measured from the healthy skin surface was recorded as the wart height. The longest length of the wart (i.e. characteristic length) as measured parallel to the healthy skin surface was recorded as the wart diameter. For example, before the treatment, the size of the wart shown in FIG. 6 was about 5.0 mm (diameter) x about 1 mm (height).

In this example, the lesion was a wart. However, any lesion is within the scope of this disclosure.

EXAMPLE 4

Device Guiding Marks on the Tissue

Forming marks external to the area occupied by a lesion is described in this example. These external marks ("device guiding marks) may be formed on the tissue surface to guide the pulse delivery device comprising the applicator tip to deliver the nanopulse electrical energy to the lesion at substantially precise locations on the wart surface. The lesion in this example is a wart. However, the external marks may be similarly formed on any lesion.

Figure 5:
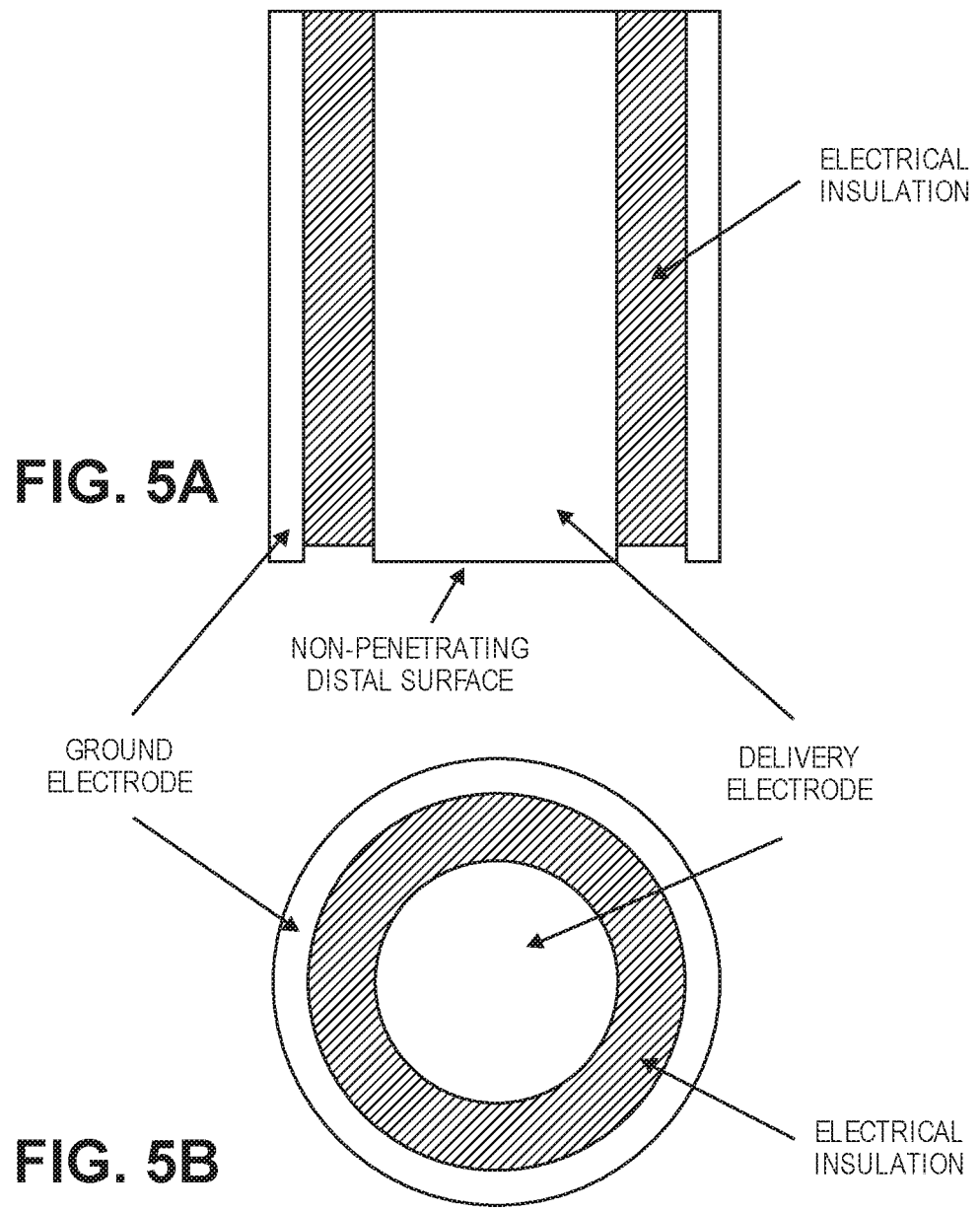
FIGS. 5A-5B: Example of a non-penetrating cylindrical distal end of the pulse delivery device: 5A longitudinal cross-sectional view and 5B radial cross-sectional view.

Parts of the applicator tip, for example, the handgrip, the electrode base, and the applicator tip collar may have diameters larger than that formed by the electrodes, as shown by way of example in FIGS. 4-5. These larger applicator parts may therefore block vision during insertion (i.e. penetration) of electrodes into the wart at desired locations and delivery of the electrical energy. When the required number of sticks (i.e. number of penetrations) is high, inserting the electrodes at desired lesion surface locations could be more difficult. If the delivery electrode is not inserted into the wart at the desired locations, the electrical energy may not be evenly delivered into the wart, which may reduce efficacy of the treatment.

Thus, the tissue surface may need to be properly marked to guide the applicator tip for single or multiple sticks, as follows.

At least one device guiding mark may be formed on the tissue surface surrounding the surface occupied by the wart by using any suitable technique. For example, these external guide marks may be formed by using a skin pen. These device guiding marks may also be formed by projecting an image of the marks onto a skin surface, for example, by using a light source and a mask.

Figure 7C:
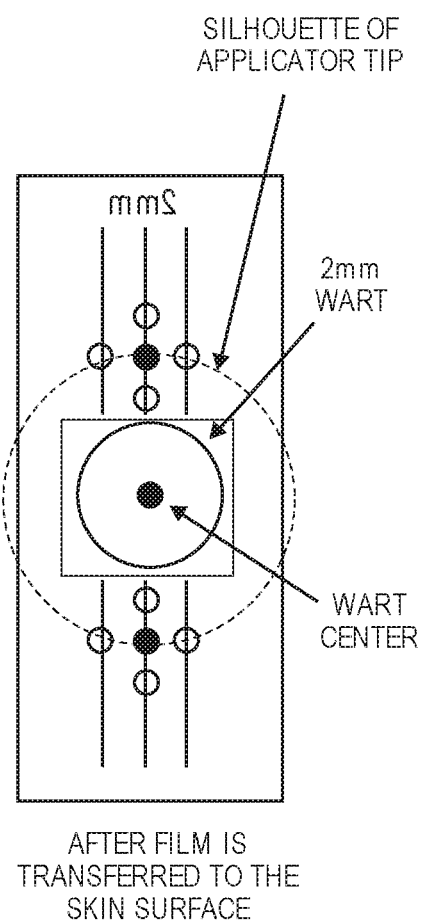

In another example, the device guiding marks may be formed by using a temporary tattoo decal. An example of a decal is shown in FIGS. 7A-7C. An example of this decal may be a temporary tattoo decal. The decal may comprise a transferable film and a device guiding mark deposited on the transferable film. The decal may have a front surface and a back surface. The decal may also have a decal boundary.

The decal may further comprise a substrate on which the transferable film may be deposited. This substrate may mechanically strengthen the transferable film and/or allow easy transfer of the transferable film to the tissue surface.

The decal may also further comprise an inscription indicating a wart diameter for which the decal would be used. The decal may have any shape. For example, the decal may be a circle, a square, a triangle or a combination thereof.

As an example, the decal shown in FIGS. 7A-7C may be used in the treatment of about 2 mm diameter warts. The device guiding marks formed on the front surface of the decal may have any suitable shape, as shown in FIG. 7A. For example, the device guiding mark may be a circle, a square, a triangle, a plus sign, a multiplication sign, a line or combinations thereof. Shapes of the external marks may be hollow shapes, solid shapes or combinations thereof. For example, the device guiding mark may be a solid circle, a hollow circle or combinations thereof. For example, the device guiding mark may be a guide line to position delivery electrode. In another example, the device guiding mark may be a solid circle guide and/or hollow circle guide to position delivery electrode.

The decal may further comprise a guide mark ("decal positioning mark") deposited on the back surface of the decal to position the decal on the skin surface for transfer of the decal's front marks onto the skin surface, as shown in FIG. 7B. The decal positioning marks on the decal's back surface may be used to position the decal on the tissue surface that includes the wart. The decal positioning marks formed on the back surface of the decal may have any suitable shape. For example, the decal positioning mark may be a circle, a square, a triangle, a plus sign, a multiplication sign, a line or combinations thereof. Shapes of the decal positioning marks may be hollow shapes, solid shapes or combinations thereof. For example, the decal positioning mark may be a solid circle, a hollow circle or combinations thereof. In another example, the decal positioning mark may be a line as shown in FIG. 7B.

The temporary tattoo decal may further comprise a marked area, as shown in FIG. 7A. The marked area may be any area that marks the boundary of the lesion on the tissue surface. This marked area may be inscribed (i.e. marked) on the decal that may be transferred to the tissue surface during application of the decal.

The marked area may also be a cut off section of the decal with no transferrable marks. That is, for example, the marked area may be free of the decal or, in other words, does not comprise the decal (or the film). The marked area may be used to position the decal on the tissue surface that includes the lesion. The marked area may have any suitable shape. For example, the decal wart boundary may be a circle, a square, a triangle, or combinations thereof.

FIG. 7C schematically shows what the marks of the decal would look like after the decal is transferred to the skin surface. An about 2 mm diameter wart, the center of the wart and a silhouette of an applicator tip are also shown in this figure to schematically demonstrate what would be observed after this transfer. (The silhouette of an applicator tip is not part of the decal and shown only for demonstrative purposes.)

Figure 8:
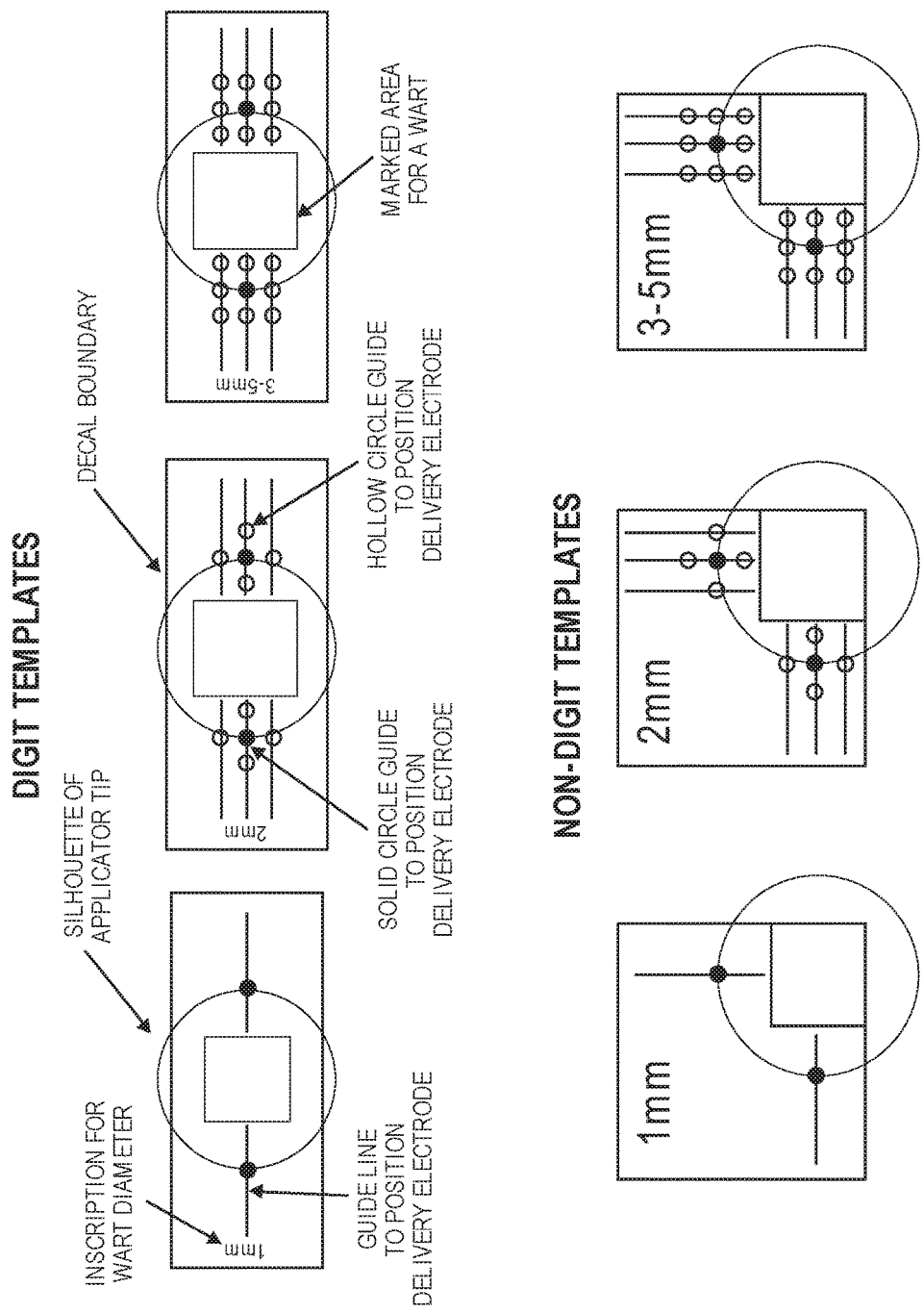
FIG. 8: Examples of temporary tattoo decals suitable for treatment of lesions on digit or non-digit tissue surfaces. The silhouette of the applicator tip is not part of the decal and shown only for demonstrative purposes.

The decal shown in FIGS. 7A-7C may be suitable for digits. Other examples of the decals are shown in FIG. 8. The size and the marking pattern may vary according to the size of the wart. Different configurations of temporary tattoo decals may be used for different types of tissue or lesion. For example, digit templates may be used for the marking of warts formed on fingers and toes. Or non-digit templates may be used for the marking of warts formed on any tissue surface. The use of digit templates may not be restricted to the digits; they may be used for non-digit tissue surfaces. Similarly, the use of non-digit templates may not be restricted to the non-digit tissue surfaces; they may be used for digit tissue surfaces.

EXAMPLE 5

Delivery of Nanopulse Electrical Energy to Lesions

The delivery of the nanopulse electrical energy to the lesions by using the markings disclosed in Example 4 is described in this example. The lesion in this example is a wart. However, the external marks may be similarly formed on any lesion.

The wart may be debrided, before the application of the nanopulse electrical energy, to remove some of the outer layers of the tissue, which may comprise dead tissue, and/or to reduce its height.

The lesion site may be cleaned using an alcohol swab and allowed to dry completely.

Figure 9:
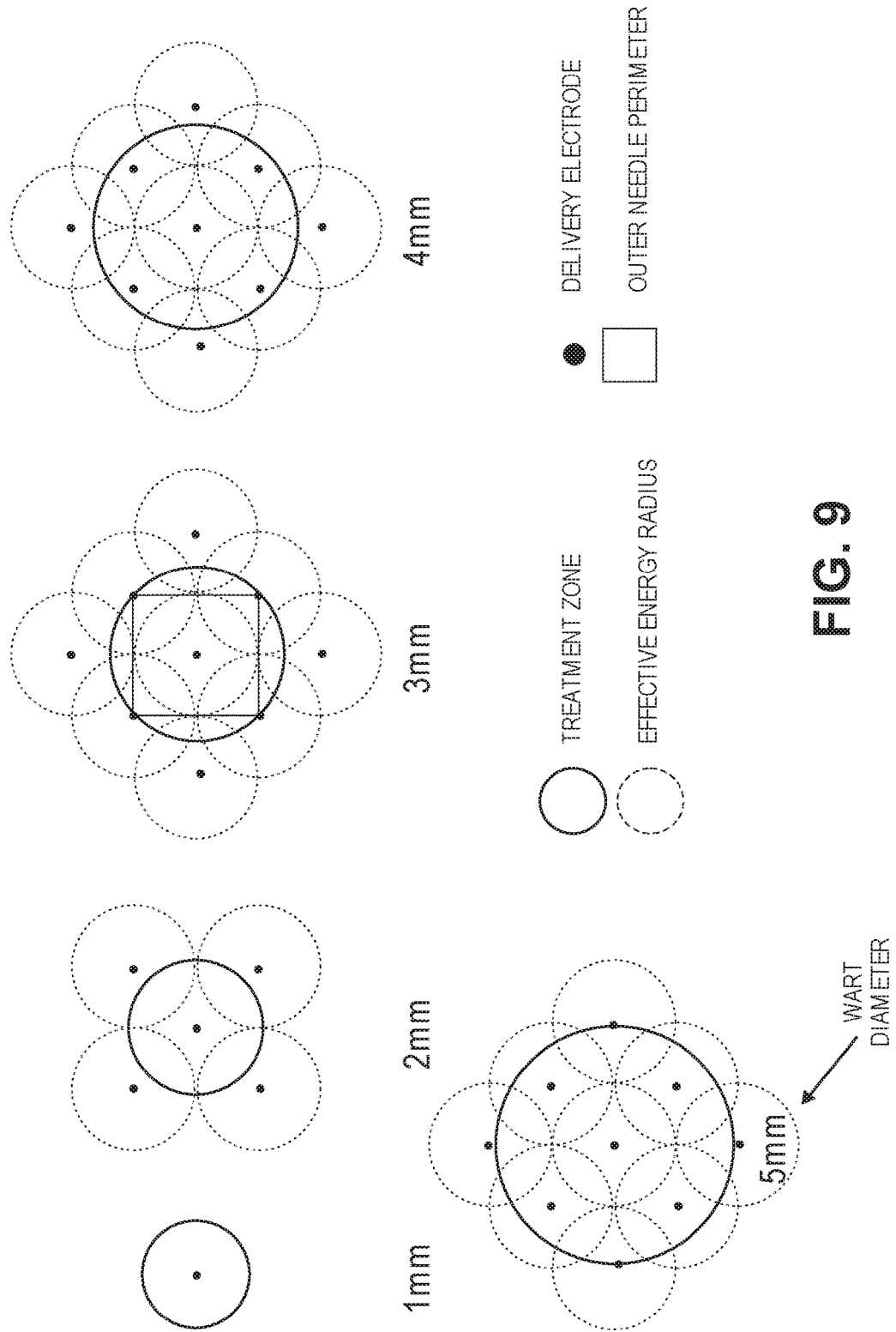
FIG. 9: Examples of lesion sizes, treatment zones and effective energy radii formed by delivery electrodes.

The number of "sticks" (i.e. penetrations of electrodes into the skin for needle electrodes or presses of substantially flat electrodes against the skin) required to treat warts that have diameters in the range of 1 mm to 5 mm diameter is described by way of example in Table 1 below and FIG. 9. Larger warts may require a greater number of sticks. A treatment zone may be formed around the wart by adding an about 1 mm wide margin to the wart radius. The required number of sticks may deliver electrical energy to the entire treatment zone. The electrode tip in this example may comprise one delivery electrode and four ground electrodes, as shown in FIG. 4. The center to center distance between the delivery electrode and the ground electrode is about 1.75 mm, which forms the effective tip radius.

TABLE 1

Wart diameter vs. required number of sticks.

| Wart Diameter (mm) | Wart Radius (mm) | Margin Width (mm) | Treatment Zone Radius (wart + margin; mm) | Effective Tip Radius (1.75 mm) | # of sticks |
| --- | --- | --- | --- | --- | --- |
| 1.00 | 0.50 | 1.00 | 1.50 | 1.75 | 1.00 |
| 2.00 | 1.00 | 1.00 | 2.00 | 1.75 | 5.00 |
| 3.00 | 1.50 | 1.00 | 2.50 | 1.75 | 9.00 |
| 4.00 | 2.00 | 1.00 | 3.00 | 1.75 | 9.00 |
| 5.00 | 2.50 | 1.00 | 3.50 | 1.75 | 9.00 |

The tissue surface at the wart center may be marked. The mark at the wart center may be used as a visual guide to form the external marks.

The tattoo (i.e. front surface guide marks) may be transferred onto the skin surface by first marking the wart center, which may be done as follows. The characteristic length of the wart may be determined, which is the longest length and thereby the diameter of the wart. Then, the approximate center of the wart, which is at half of the characteristic length, may be marked by using a skin pen. If an anesthetic is injected to the wart before the delivery of the electrical energy, this marking may be done after the anesthetic is injected. This mark may also be used to guide the delivery electrode for the first insertion of the applicator tip into the wart.

A local anesthetic may be injected to the tissue before the application of the electrical energy. The local anesthetic may be injected before or after the application of the temporary tattoo decal on the lesion surface. The approximate center of the wart prior to injection of the local anesthetic may be marked by using a skin pen.

For formation of the device guiding marks on the tissue surface, first a decal may be selected that is suitable for the type of tissue and the type of lesion. Then, the decal may be placed on the surface of the tissue and positioned around the wart by using the decal positioning marks on the back surface of the decal. A moist article, such as towel or sponge, may be applied to the decal for about 10 seconds. Finally, the moist article may be lifted and the decal substrate (i.e. backing material) may be removed, leaving the external guide marks on the tissue (i.e. skin in this example).

To avoid formation of air pockets between the electrodes, both the lesion and the electrodes may be covered with Aquasonic 100 ultrasound transmission gel (Parker Laboratories Inc., Fairfield, N.J., USA). A small amount of the gel may be applied to the cleaned skin at the site intended for applicator tip placement. A small amount of the gel may also be applied to the electrodes. These gel applications may be carefully carried out to prevent or minimized formation of air bubbles in the gel.

The amount of electrical energy delivered to the lesion may vary with lesion size. For example, for warts with a diameter of about 1 mm or less, at least one group of pulses may be delivered per treatment visit. Each group of pulses may comprise at least one electrical nanopulse. In another example, for warts with a diameter larger than 1 mm, or 2 mm or less; at least 5 groups of pulses may be delivered per treatment visit. Yet, in another example, for warts with a diameter larger than 2 mm, or 5 mm or less; at least 9 groups of pulses may be delivered per treatment visit. Each group of pulses form an application, which comprises at least one electrical pulse.

Figure 10:
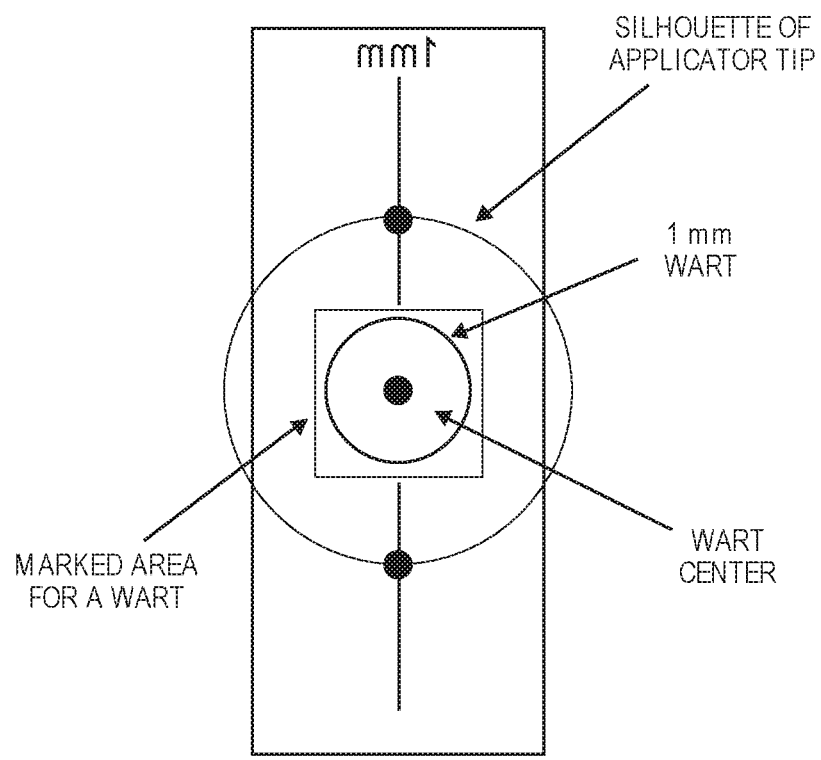
FIG. 10: Example of a temporary tattoo decal after it is transferred on a digit tissue surface that has about 1 mm lesion. The silhouette of the applicator tip is not part of the decal and shown only for demonstrative purposes.

The electrical energy may be delivered to the lesion by using the pulse delivery device as follows. For example, for warts with a diameter of about 1 mm or less, the electrodes may penetrate into the lesion only once. As shown in FIG. 10, to deliver electrical nanopulses to the tissue at the wart center, the applicator tip's collar (schematically shown as "silhouette of the applicator tip") may be aligned with the two solid circular external guide marks of the transferred decal. Then, the electrodes may be inserted into the wart and the electrical energy may be delivered after the insertion. This example was described for the lesion formed on a digit. However, the same procedure may be carried out for the non-digit lesions.

Figure 11:
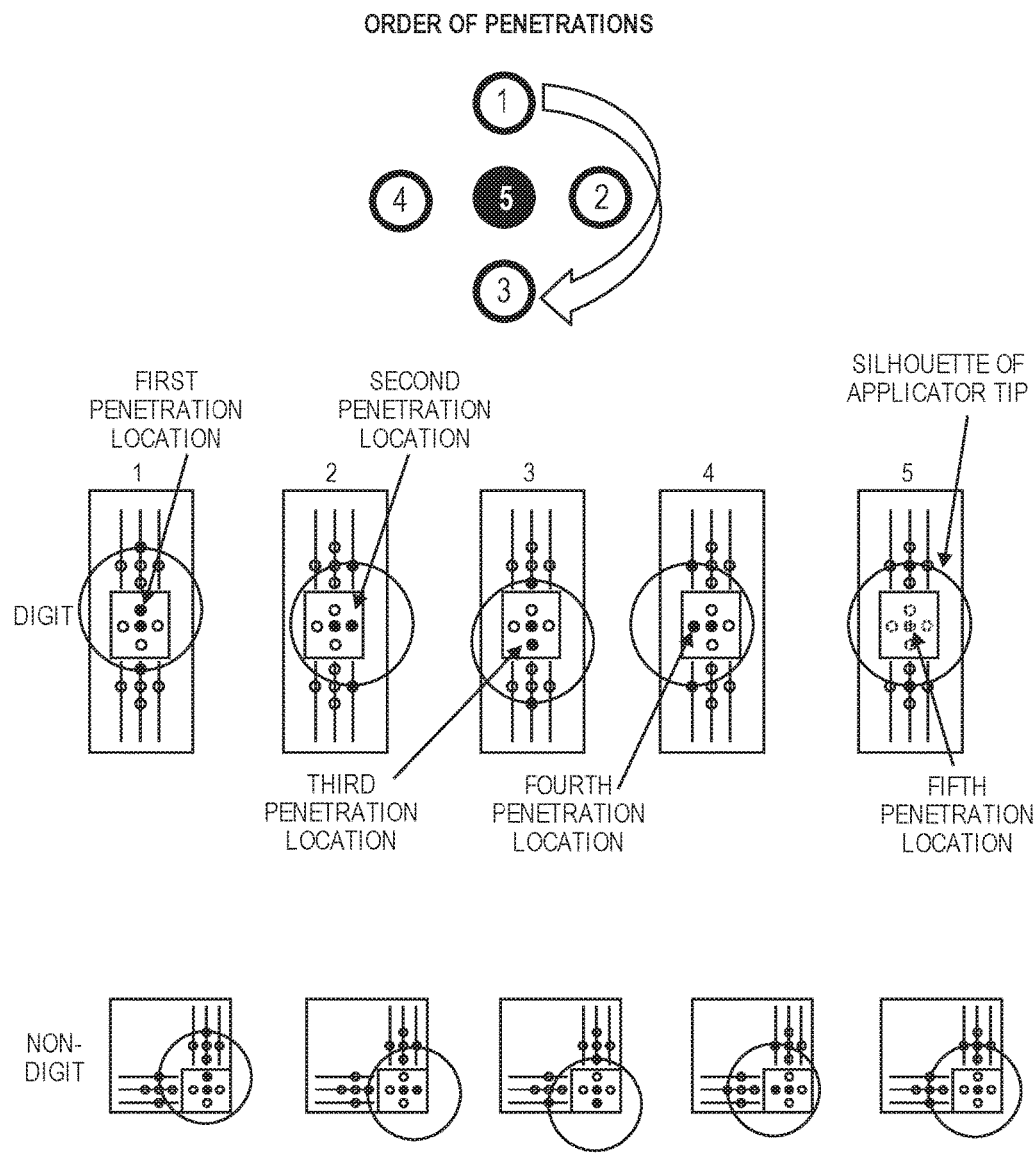
FIG. 11: Example of a treatment pattern for lesions with diameters varying in the range of 1 mm to 2 mm. The silhouette of the applicator tip is not part of the decal and shown only for demonstrative purposes.

In another example, for warts with a diameter larger than 1 mm, or 2 mm or less; the electrodes may penetrate into the lesion 5 times. The penetration procedure is shown in FIG. 11. First, electrode penetration may be carried out by aligning the applicator tip's collar with the circular device guiding marks of the transferred film, highlighted as two solid circles, shown in FIG. 11-1. This may deliver the electrical nanopulses to the lesion location marked with a solid circle within the decal boundary. Then, the second electrode penetration may be carried out by aligning the applicator tip's collar with the circular device guiding marks of the transferred film, highlighted as two solid circles, shown in FIG. 11-2. This may deliver the electrical nanopulses to the lesion location marked with a solid circle within the decal boundary. The remaining three penetrations may be similarly carried out.

Figure 12:
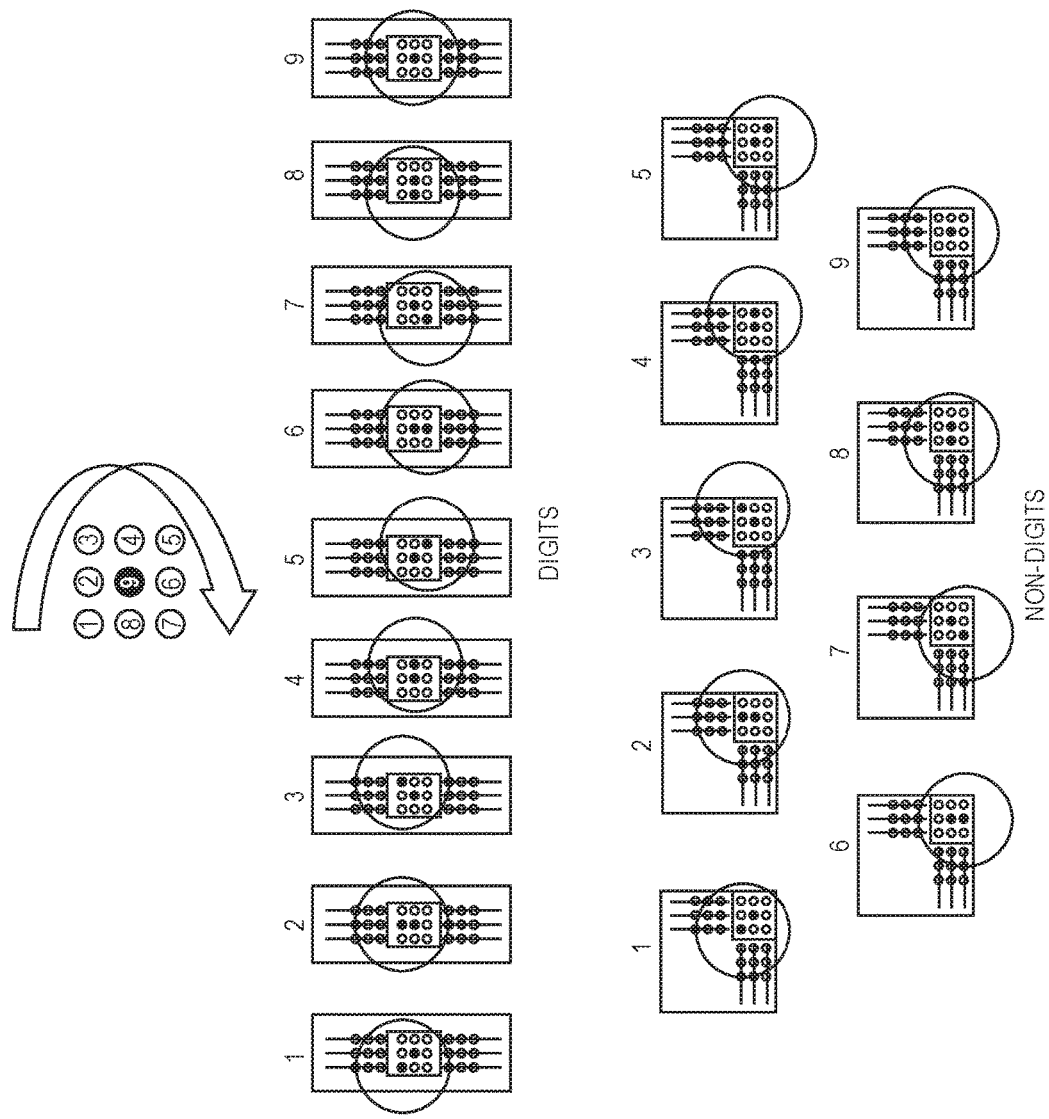
FIG. 12: Example of a treatment pattern for lesions with diameters varying in the range of 2 mm to 5 mm. The silhouette of the applicator tip is not part of the decal and shown only for demonstrative purposes.

In another example, for warts with a diameter larger than 2 mm, or 5 mm or less; the electrodes may penetrate into the lesion at least 9 times. The penetration procedure is shown in FIG. 12. First electrode penetration may be carried out by aligning the applicator tip's collar with the circular device guiding marks of the transferred decal, highlighted as two solid circles, as shown in FIG. 12-1. This may deliver the electrical nanopulses to the lesion location marked with a solid circle within the decal boundary. Then, the second electrode penetration may be carried out by aligning the applicator tip's collar with the circular device guiding marks of the transferred tattoo decal, highlighted as two solid circles, as shown in FIG. 12-2. This may deliver the electrical nanopulses to the lesion location marked with a solid circle within the decal boundary. The remaining seven penetrations may be similarly carried out.

In this example, the treatment of lesions is carried out by using the needle type electrodes shown in FIGS. 5A-5B. This is only for demonstrative purposes. The treatment procedure described above may similarly be carried out with any other type of electrode (or applicator tip) design such as, for example, the flat tip design shown in FIG. 6.

EXAMPLE 6

Device Alignment Mark On The Applicator Tip

Figure 13:
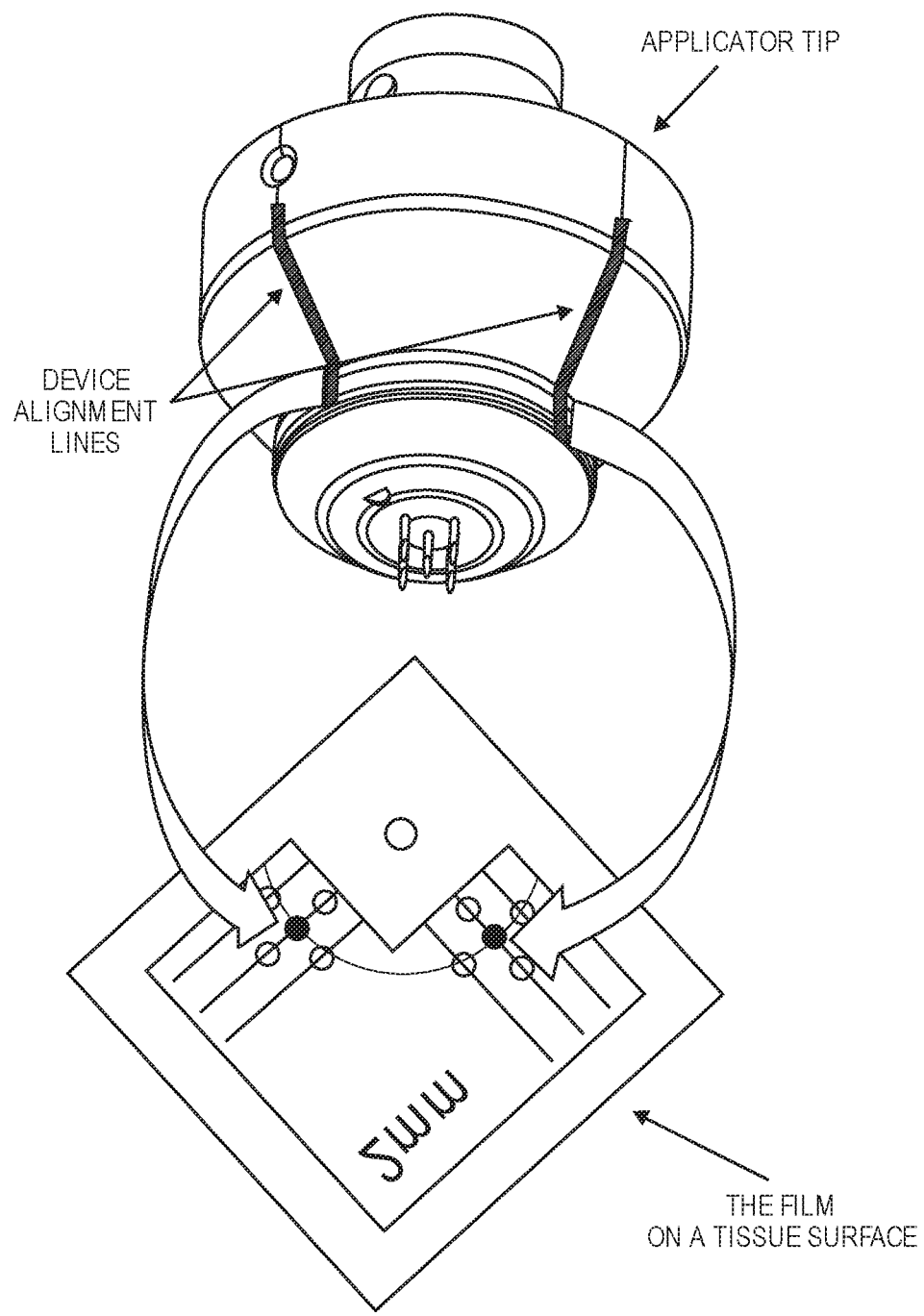
FIG. 13: Example of an applicator tip with guide lines and how these guide lines may be used to align the applicator tip guidelines with the external marks on the tissue surface formed by the temporary tattoo decal.

In another example, the applicator tip may also have marks to guide the applicator tip to deliver electrical nanopulses to the tissue at substantially precise tissue locations. An example of such marking is shown in FIG. 13. In this example, the guide marks ("device alignment marks") on the applicator tip are lines. However, any type of guide marks may be used. Examples of such applicator tip guide marks may be solid or hollow circles, dashed or solid lines, or combinations thereof. These device alignment marks may be used in combination with the decal marks, as shown in FIG. 13.

Any combination of above systems, devices, and methods are within the scope of this disclosure.

Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain.

All articles, patents, patent applications, and other publications that have been cited in this disclosure are incorporated herein by reference.

In this disclosure, the indefinite article "a" and phrases "one or more" and "at least one" are synonymous and mean "at least one".

The phrase "means for" when used in a claim is intended to and should be interpreted to embrace the corresponding structures and materials that have been described and their equivalents. Similarly, the phrase "step for" when used in a claim is intended to and should be interpreted to embrace the corresponding acts that have been described and their equivalents. The absence of these phrases from a claim means that the claim is not intended to and should not be interpreted to be limited to these corresponding structures, materials, or acts, or to their equivalents.

The scope of protection is limited solely by the claims that now follow. That scope is intended and should be interpreted to be as broad as is consistent with the ordinary meaning of the language that is used in the claims when interpreted in light of this specification and the prosecution history that follows, except where specific meanings have been set forth, and to encompass all structural and functional equivalents.

Relational terms such as "first" and "second" and the like may be used solely to distinguish one entity or action from another, without necessarily requiring or implying any actual relationship or order between them. The terms "comprises," "comprising," and any other variation thereof when used in connection with a list of elements in the specification or claims are intended to indicate that the list is not exclusive and that other elements may be included. Similarly, an element preceded by an "a" or an "an" does not, without further constraints, preclude the existence of additional elements of the identical type.

None of the claims are intended to embrace subject matter that fails to satisfy the requirement of Sections 101, 102, or 103 of the Patent Act, nor should they be interpreted in such a way. Any unintended coverage of such subject matter is hereby disclaimed. Except as just stated in this paragraph, nothing that has been stated or illustrated is intended or should be interpreted to cause a dedication of any component, step, feature, object, benefit, advantage, or equivalent to the public, regardless of whether it is or is not recited in the claims.

The abstract is provided to help the reader quickly ascertain the nature of the technical disclosure. It is submitted with the understanding that it will not be used to interpret or limit the scope or meaning of the claims. In addition, various features in the foregoing detailed description are grouped together in various embodiments to streamline the disclosure. This method of disclosure should not be interpreted as requiring claimed embodiments to require more features than are expressly recited in each claim. Rather, as the following claims reflect, inventive subject matter lies in less than all features of a single disclosed embodiment. Thus, the following claims are hereby incorporated into the detailed description, with each claim standing on its own as separately claimed subject matter.

The invention claimed is:

1. A system comprising:
   a pulse delivery device comprising at least one delivery electrode; and
   a decal configured for assisting in positioning the pulse delivery device on a surface of an object, the decal comprising:
      a film that is transferable to a region on the surface of the object; and
      a device guiding mark on the film that is transferable to the object surface together with the film and that is usable to position the pulse delivery device in relation to the object surface;
      wherein the film and the device guiding mark are configured to detachably attach to the object surface after the film is transferred to the object surface,
   wherein the pulse delivery device is configured to deliver at least one electrical pulse to the region after the film is transferred to the object surface; and
   wherein a distal end of the at least one delivery electrode is configured to pass through the film at the device guiding mark to be in contact with the region on the object surface.

2. The system of claim 1, wherein the decal further comprises a substrate to which the film is detachably attached before the film is transferred to the object surface.

3. The system of claim 1, further comprising a decal positioning mark that is usable to position the decal on the object surface, wherein the decal positioning mark is on a back surface of the decal.

4. The system of claim 1, wherein the object is a skin and the region comprises a skin lesion.

5. The system of claim 4, wherein the skin lesion is a wart of a human.

6. The system of claim 1, wherein the pulse delivery device further comprises a device alignment mark, the device alignment mark being usable with the device guiding mark to position the at least one delivery electrode in relation to the region before delivery of at least one electrical pulse.

7. The system of claim 6, wherein the device alignment mark is a part of the at least one delivery electrode.

8. The system of claim 1, wherein the decal further comprises an inscription indicating a size of the region.

9. The system of claim 1, wherein the system further comprises a power supply, a controller, and a pulse generator, wherein:
   the power supply provides electrical power to both the controller and the pulse generator;
   the controller provides control signals to both the controller and the pulse generator; and
   the pulse generator generates at least one electrical pulse with a duration of no longer than 1,000 nanoseconds at full-width-at-half-maximum and delivers the at least one electrical pulse to the pulse delivery device.

10. The system of claim 1, wherein the decal comprises a marked area configured and sized to indicate a boundary around the region on the object surface.

11. The system of claim 10, wherein the pulse delivery device further comprises at least one ground electrode; wherein both the at least one delivery electrode and the at least one ground electrode have distal ends; and wherein the device guiding mark and the marked area on the decal are configured such that, after the device guiding mark and marked area on the decal are transferred to the object, the device guiding mark and marked area on the decal are aligned with the distal ends of the at least one delivery electrode and the at least one ground electrode, when the distal ends are brought in contact with the region on the object surface.

12. The system of claim 10, wherein the marked area is a cut off section of the decal and does not comprise a film.

13. The system of claim 1, wherein the decal is selected based on a type and a size of the region.

14. The system of claim 1, wherein the decal has a front surface and a back surface, the film has a front surface and a back surface, and wherein the front surface of the film is configured to be in contact with the region on the object surface after the film is transferred to the object surface.

15. A system comprising:
   a pulse delivery device comprising an applicator tip and at least one delivery electrode; and
   a decal configured for assisting in positioning the pulse delivery device on a surface of an object, the decal comprising:
      a film that is transferable to a region on the surface of the object, the region having a size corresponding to a treatment zone;
      a marked area on the film configured to indicate a boundary around the region after the film is transferred to the object surface; and
      at least one device guiding mark on the film that is transferable to the object surface together with the film and that is usable to position the pulse delivery device in relation to the object surface,
      wherein the film, the marked area and the at least one device guiding mark are configured to detachably attach to the object surface after the film is transferred to the object surface,
   wherein the pulse delivery device is configured to deliver at least one electrical pulse to the region after the film is transferred to the object surface; and
   wherein the at least one device guiding mark and the marked area indicating the boundary around the treatment zone are configured such that, after the at least one device guiding mark and the marked area are transferred to the object surface, when the applicator tip is aligned with the at least one device guiding mark, a distal end of the at least one delivery electrode is positioned inside an area defined by the marked area when brought in contact with the region on the object surface.

16. The system of claim 15, wherein the object is a skin and the region comprises a skin lesion.

17. The system of claim 15, wherein the decal is selected based on a type and the size of the region.

18. The system of claim 15, wherein a marking pattern on the decal is based on a type and the size of the region.

19. The system of claim 15, wherein the device guiding mark comprises any one or more of the following: a circle, a square, a triangle, a plus sign, a line, or a combination thereof.

20. The system of claim 15, wherein the marked area is a cut off section of the decal free of film.

21. The system of claim 15, wherein the applicator tip comprises at least one device alignment mark.

22. The system of claim 21, wherein the at least one device alignment mark comprises one or more of the following: a solid circle, a hollow circle, a dashed line, a solid line, or combination thereof.

23. The system of claim 15, the system comprises a pulse generator configured to generate and deliver one or more electrical pulses to the pulse delivery device.

24. A system comprising:
- a pulse delivery device comprising an applicator tip having at least one delivery electrode and at least one device alignment line; and
- a decal configured for assisting in positioning the pulse delivery device on a surface of an object, the decal comprising:
  - a film that is transferable to a region on the surface of the object;
  - at least one device guideline on the film that is transferable to the object surface together with the film and that is usable to position the pulse delivery device in relation to the object surface, the film and the device guiding mark are configured to detachably attach to the object surface after the film is transferred to the object surface, wherein the pulse delivery device is configured to deliver at least one electrical pulse to the region after the film is transferred to the object surface; and wherein the at least one device alignment line of the applicator tip is usable with the device guideline of the film to orient the applicator tip and position a distal end of the at least one delivery electrode in relation to the region before delivery of at least one electrical pulse.

* * * * *